US010959406B2

(12) United States Patent
Campbell et al.

(10) Patent No.: US 10,959,406 B2
(45) Date of Patent: Mar. 30, 2021

(54) ANIMAL TRAINING AIDS AND TOYS

(71) Applicant: My Clever Dog Pty Ltd., Largs Bay (AU)

(72) Inventors: George Giles Campbell, Brighton (AU); Justin Anthony Daley, Largs Bay (AU)

(73) Assignee: MY CLEVER DOG PTY LTD, Largs Bay (AU)

( * ) Notice: Subject to any disclaimer, the term of this patent is extended or adjusted under 35 U.S.C. 154(b) by 506 days.

(21) Appl. No.: 14/906,134

(22) PCT Filed: Feb. 27, 2015

(86) PCT No.: PCT/AU2015/000112
§ 371 (c)(1),
(2) Date: Jan. 19, 2016

(87) PCT Pub. No.: WO2015/127502
PCT Pub. Date: Sep. 3, 2015

(65) Prior Publication Data
US 2016/0174527 A1    Jun. 23, 2016

(30) Foreign Application Priority Data

Feb. 27, 2014    (AU) .................................. 2014900641

(51) Int. Cl.
*A01K 15/02*    (2006.01)
(52) U.S. Cl.
CPC ............ *A01K 15/02* (2013.01); *A01K 15/025* (2013.01); *A01K 15/026* (2013.01); *A61L 2209/133* (2013.01)
(58) Field of Classification Search
CPC .... A01K 15/025; A01K 15/026; A01K 15/02; A61L 2209/133
See application file for complete search history.

(56) References Cited

U.S. PATENT DOCUMENTS 2,086,631 A    7/1937    Munro
3,126,869 A    3/1964    Young et al.
(Continued)

FOREIGN PATENT DOCUMENTS

CN    1631451    6/2005
CN    202232504 U    5/2012
(Continued)

OTHER PUBLICATIONS

Extended European Search Report for PCT/AU2015/000112 dated Sep. 22, 2017.
(Continued)

*Primary Examiner* — Jessica B Wong
(74) *Attorney, Agent, or Firm* — FisherBroyles, LLP; Craig W. Mueller

(57) ABSTRACT

The invention provides an animal training aid or to for use in scent based animal training or activities. The aid or toy comprises: a housing comprising an interior cavity configured to contain a scented material that releases substantially no scent that is desirable to the animal in an unactivated state and releases a scent that is desirable to the animal in an activated state; one or more vents on an external surface of the housing, each vent in communication with the interior cavity so that a scent from the scented material can be released from the interior cavity to the exterior of the housing where it can be detected by the animal; and an activator for activating the scented material from the unactivated state to the activated state, the activator being operable from the external surface of the housing.

17 Claims, 14 Drawing Sheets

(56) References Cited

U.S. PATENT DOCUMENTS

| | | |
|---|---|---|
| 4,928,632 A | 5/1990 | Gordon |
| 5,037,343 A | 8/1991 | Benites |
| 5,865,146 A | 2/1999 | Markham |
| 6,415,741 B2 | 7/2002 | Suchowski et al. |
| 6,531,145 B1 | 3/2003 | Reichert |
| 7,146,934 B1 | 12/2006 | Staley |
| 8,464,665 B1 | 6/2013 | Scheffler et al. |
| 8,522,725 B1 | 9/2013 | Moore |
| 2004/0244719 A1 | 12/2004 | Jager |
| 2006/0054106 A1 | 3/2006 | Renforth |
| 2009/0277396 A1 | 11/2009 | Shatoff et al. |
| 2011/0146588 A1 | 6/2011 | Ward |
| 2012/0047996 A1 | 3/2012 | Reese |
| 2012/0318210 A1 | 12/2012 | Anderson |
| 2013/0055965 A1 | 3/2013 | Valle et al. |
| 2014/0193764 A1* | 7/2014 | Pizzini ............... A61M 11/041 432/247 |

FOREIGN PATENT DOCUMENTS

| | | |
|---|---|---|
| CN | 202285807 | 7/2012 |
| CN | 202565946 U | 12/2012 |
| CN | 203040391 | 7/2013 |
| GB | 2492110 A | 12/2012 |
| WO | 19960037098 A1 | 11/1996 |
| WO | 9852424 A1 | 11/1998 |
| WO | 20060058285 A2 | 6/2006 |
| WO | 2013043581 | 3/2013 |

OTHER PUBLICATIONS

Chinese Office Action issued in Chinese Patent Application No. 2015800206844 dated Feb. 27, 2015, 12 pgs.

EP Examination Report issued in EP Patent Application 15755427.0 dated Jun. 28, 2018, 5 pgs.

EP Second Examination Report issued in EP Patent Application 15755427.0 dated Sep. 9, 2018, 8 pgs.

English Abstract—CN1631451A.

English Abstract—CN202285807U.

English Abstract—CN203040391 U.

English translation of CN 202565946 from Google Patents found at: https://www.google.com/patents/CN202565946U?cl=en&dq=CN+202565946&hl=en&sa=X&ved=0CB8Q6AEwAGoVCMlkqfosbGSxglVBZSIlCh0yYQD9.

English translation of CN 202232504 from Google Patents found at: https://www.google.com/patents/CN202232504U?cl=en&dq=CN+202232504&hl=en&sa=X&ved=0CB8Q6AEwAGoVChMlwJKagrKSxglVRy6lCh0UUQaG.

* cited by examiner

ANIMAL TRAINING AIDS AND TOYS

PRIORITY DOCUMENTS

The present application claims priority from Australian Provisional Patent Application No. 2014900641 titled "ANIMAL TRAINING AIDS AND TOYS" and filed on 27 Feb. 2014, the content of which is hereby incorporated by reference in its entirety.

TECHNICAL FIELD

The present invention relates to a devices and systems for use in scent based training and activities with an animal such as a dog.

BACKGROUND

Training of companion, hunting and working animals is commonplace. Training involves modifying the behaviour of an animal either to assist in specific activities or undertake particular tasks, or to participate effectively in domestic life. For ease, further discussion herein will relate to training of dogs. However, it will be appreciated that the matters discussed could also be used or applied to the training of other animals.

Dogs are able to learn by classical conditioning in which they form an association between two stimuli, by non-associative learning whereby their behaviour is modified through habituation or sensitisation, or by operant conditioning whereby they associate a behaviour with a consequence.

There are a variety of established methods of dog training. Some of the better known are the Koehler method, clicker training, dominance-based training, and relationship-based training. The common characteristics of successful methods are knowing the dog's attributes and personality, accurate timing of reinforcement and/or punishment and consistent communication.

Dogs have an acute sense of smell and, therefore, scents can be used as part of a dog training program to lure the dog toward an object or person, or to reward the dog for a particular behaviour. For this reason, scent based dog training devices and toys are known. U.S. Pat. No. 6,531,145 discloses silica gel beads that conveniently release scent for use in training dogs to hunt using scent. Chew toys have been disclosed that contain a scent component in their manufacture to make them more attractive to dogs. One example is U.S. Pat. No. 6,415,741, a scented chew toy that allows the scented material to be inserted within the body of the chew toy during manufacture.

Other than for training, scents can also be used to pacify or reward animals.

A problem with many known scent based training aids and toys is the scent is not renewable and, as a consequence, the scent based aspect of the aid or toy has a limited life. There is a need for a training aid or toy in which the scent is replaceable. There is also a need for a training aid or toy in which the user can control how much scent is released from the aid or toy and/or when the scent is released from the aid or toy.

SUMMARY

According to a first aspect, there is provided an animal training aid or toy comprising:

a housing comprising an interior cavity configured to contain a scented material;

one or more vents on an external surface of the housing, each vent in communication with the interior cavity so that a scent from the scented material can be released from the interior cavity to the exterior of the housing; and means for controlling the amount of scent released from the scented material.

The means for controlling the amount of scent released from the scented material may be an activator for activating the scented material from an external surface of the housing.

Thus, according to a second aspect, there is provided an animal training aid or toy comprising:

a housing comprising an interior cavity configured to contain a scented material that releases substantially no scent that is desirable to the animal in an unactivated state and releases a scent that is desirable to the animal in an activated state;

one or more vents on an external surface of the housing, each vent in communication with the interior cavity so that a scent from the scented material can be released from the interior cavity to the exterior of the housing where it can be detected by the animal; and an activator for activating the scented material from the unactivated state to the activated state, the activator being operable from the external surface of the housing.

In certain embodiments, the animal training aid or toy further comprises attachment means for removably attaching the housing to a substrate or device such as a wrist band or toy.

In certain embodiments, the housing comprises a plurality of housing parts that are separable from one another to allow the scented material to be introduced or removed from the interior cavity.

In certain embodiments, the scented material is a solid having a liquid scent imbibed therein or thereon. The solid may be in the form of a disc.

According to a second aspect, there is provided a method for training animals using primary reinforcement to reinforce desired animal behaviour, the method comprising: providing an animal training aid or toy in accordance with the second aspect of the invention; activating the scented material in the aid or toy; and providing a reward to the animal simultaneously with, or immediately following, a desired behaviour by providing the animal with the aid or toy.

BRIEF DESCRIPTION OF DRAWINGS

Embodiments of the present invention will be discussed with reference to the accompanying drawings wherein.

In the following description, like reference characters designate like or corresponding parts throughout the figures.

DESCRIPTION OF EMBODIMENTS

Figure 26:
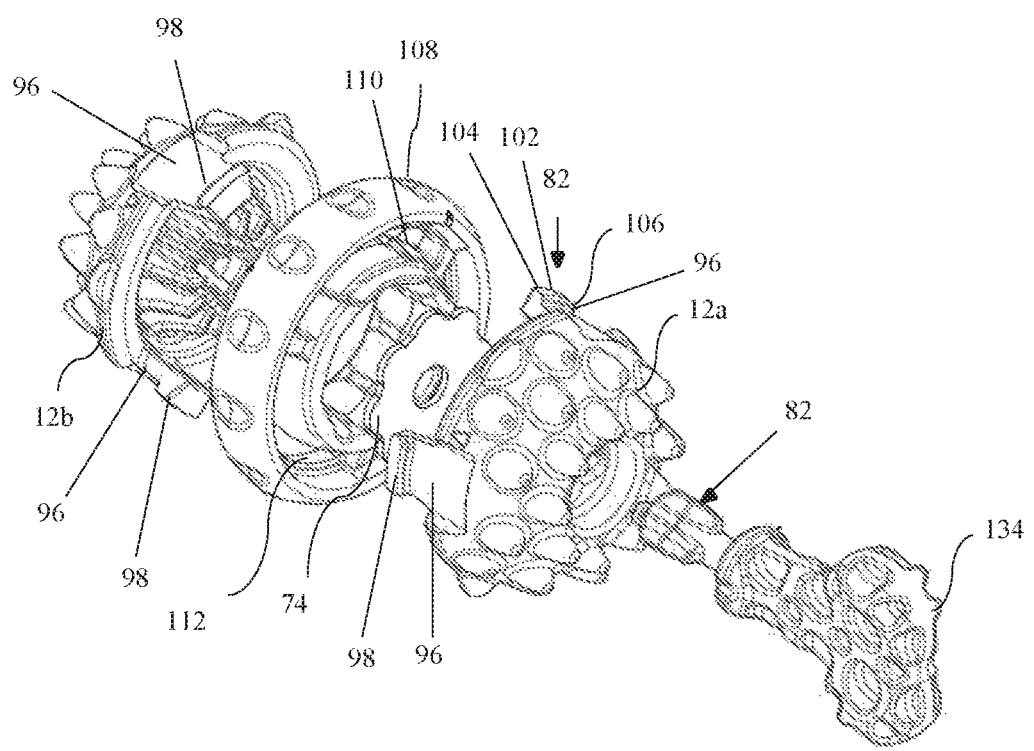
FIG. 26 is an exploded isometric view of an animal training aid or toy in accordance with a still further embodiment of the invention.

FIGS. 1 to 9 show an embodiment of an animal training aid or toy 10 in accordance with the invention. FIGS. 10 to 21 show a further embodiment of an animal training aid or toy 10 in accordance with the invention. Another embodiment of an animal training aid or toy 10 in accordance with the invention is shown in FIGS. 22 to 25, and still a further embodiment of an animal training aid or toy 10 in accordance with the invention is shown in FIG. 26.

The animal training aid or toy 10 is suitable for use in scent based animal training or activities. The scent may be a scent that is desirable to an animal such that the training aid can be used in reward based training or the toy can be used in general activities with the animal. The scent could also be a scent that pacifies or soothes an animal in which case the toy 10 could be used in bedding or similar or could be used as a training aid to assist in pacifying an animal.

The animal training aid or toy 10 comprises a housing 12 comprising an interior cavity 14 configured to contain a scented material. The aid or toy 10 also comprises one or more vents 18 on an external surface 20 of the housing 12. Each vent 18 is in communication with the interior cavity 14 so that a scent from the scented material can be released from the interior cavity to the exterior of the housing. The device also comprises means 22 for controlling the amount of scent released from the scented material.

The aid or toy 10 comprises a housing 12 comprising an interior cavity 14 (best seen in FIGS. 7, 13, 14 and 25) configured to contain a scented material 16. The scented material 16 releases substantially no scent that is desirable to the animal in an unactivated state and releases a scent that is desirable to the animal in an activated state. As used herein, the term "releases substantially no scent that is desirable to the animal in an unactivated state" does not mean that the scented material releases no scent detectable by the animal in the activated state. Rather, in the activated state substantially more scent is released from the scented material than in the unactivated state. For example, in embodiments that are described in more detail later, the scented material 16 comprises scent that is microencapsulated and deposited on a substrate surface. In practice, some of the microencapsulated particles may be disrupted when the scented material 16 is placed in the interior cavity 14. However, substantially more scent is subsequently released when the scented material 16 is activated. The scented material 16 is fixed in the interior cavity 14 and is not released from the interior cavity 14 during the normal course of animal activity with the aid or toy 10.

The aid or toy 10 also comprises one or more vents 18 open to an exterior surface 20 of the housing. Each vent 18 is in communication with the interior cavity 14 so that a scent from the scented material 16 can be released from the interior cavity 14 to the exterior of the housing 12 where it can be detected by the animal. Whilst in the illustrated embodiments the vents 18 are in the form of paths or bores that are specifically provided for the purpose of allowing scent from the scented material to be released from the interior cavity to the exterior of the housing, the vent(s) 18 could be any form of opening, gap, aperture or similar that provides a path for the scent to pass from the interior cavity 14 to the exterior of the housing 12. For example, the vents 18 may be in the form of a gap between two parts of the aid or toy 10. It will be appreciated that only a very small gap is required to allow volatile components of the scented material 16 to exit from the interior cavity 14. It is contemplated that the vents may be normally closed when the aid or toy 10 is in its normal state but may be opened when an animal or user changes the configuration of the aid or toy 10, such as by chewing the aid or toy.

The aid or toy 10 also comprises an activator 22 (best seen in FIGS. 3 and 17 to 20) for activating the scented material 16 from the unactivated state to the activated state, the activator 22 being operable from the external surface 20 of the housing 12. The activator 22 can be any device or form that is capable of physically disrupting the scented material 16 so that scent is released therefrom. In the illustrated embodiments, the activator 22 is generally in the form of ribs that contact the surface of a solid scented material 16 to disrupt the surface thereof and allow volatile scents to be released or to increase the amount of volatile scents released. In other forms, the activator is can be used to pierce or crush a capsule containing a liquid scented material 16 so that the capsule is opened and the scented liquid or oil is released therefrom. In still other forms, the activator may be in the form of protrusions, extensions, needles, and the like in or adjacent the interior cavity 14 that are able to physically disrupt the scented material 16 when an external stimulus, such as an animal biting or a user squeezing, is applied to the aid or toy 10 to thereby allow volatile scents to be released or to increase the amount of volatile scents released.

The aid or toy 10 shown in FIGS. 1 to 21 and 26 is generally in the shape of a ball and can be used as a stand-alone toy for ball-type activities with an animal. The aid or toy 10 shown in FIGS. 22 to 25 is in the form of two balls each of which can be attached to a substrate or device as described in more detail later. It is contemplated that the aid or toy 10 can take any shape desired. The shape of the aid or toy 10 may be dictated by the end use of the aid or toy and, in cases where the aid or toy 10 is specifically used as an aid for attachment to a wrist band for example, the aid 10 may be in the form of a small, circular, low-profile container.

In the embodiment illustrated in FIGS. 1 to 9, the housing 12 is a unitary construction and comprises a central bore 24 that extends from the exterior surface 20 at one area of the ball to the exterior surface 20 at another area of the ball. In the illustrated embodiments, the bore 24 extends diametrically through the housing 12. In these embodiments, the exterior surface 20 of the housing 12 comprises a plurality of ridges 26 and valleys 28 that assist a handler or the animal with gripping the aid or toy 10. Other decorative or functional forms could be included on the exterior surface 20.

In the embodiment illustrated in FIGS. 1 to 9, the toy 10 also comprises a plug and cap assembly 30 that fits into the central bore 24 and is used to retain the scented material 16 in the interior cavity 14 in the central bore 24. The plug and cap assembly 30 comprises a plug 32 and a cap 34. The plug 32 and cap 34 are configured to reversibly fit together. In an assembled form, the plug 32 and cap 34 together form an interior cavity 14 into which the scented material 16 is fitted.

Figure 1:
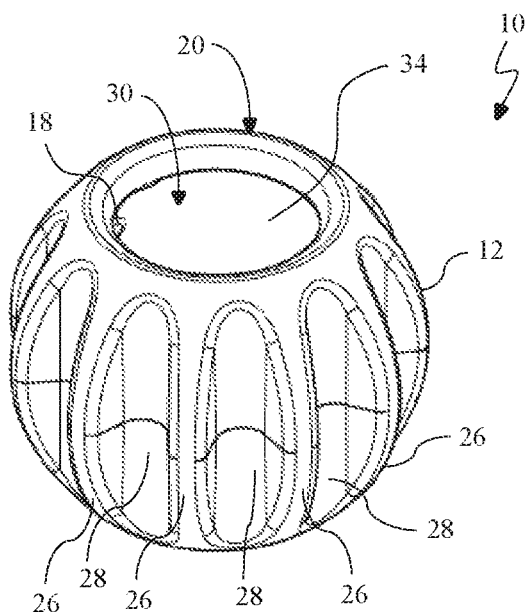
FIG. 1 is an isometric view of an animal training aid or toy in accordance with an embodiment of the invention.
Figure 2:
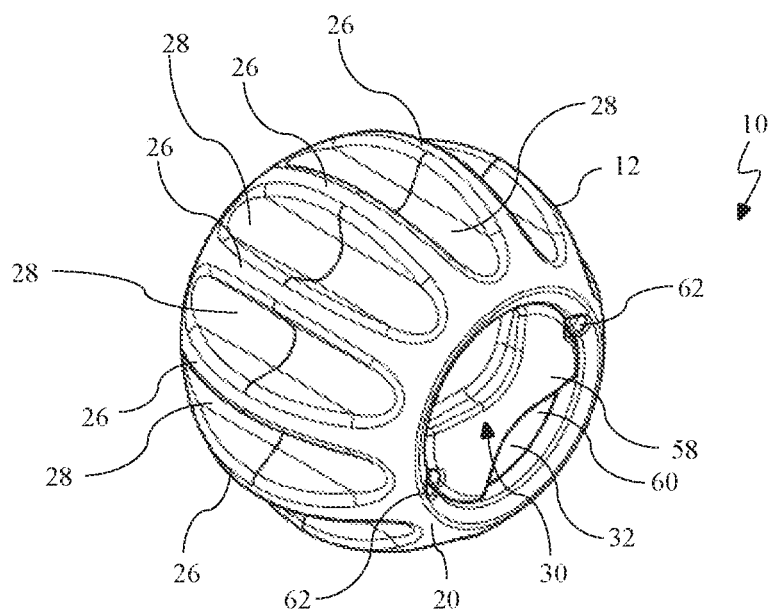
FIG. 2 is an isometric view of an animal training aid or toy in accordance with an embodiment of the invention.
Figure 3:
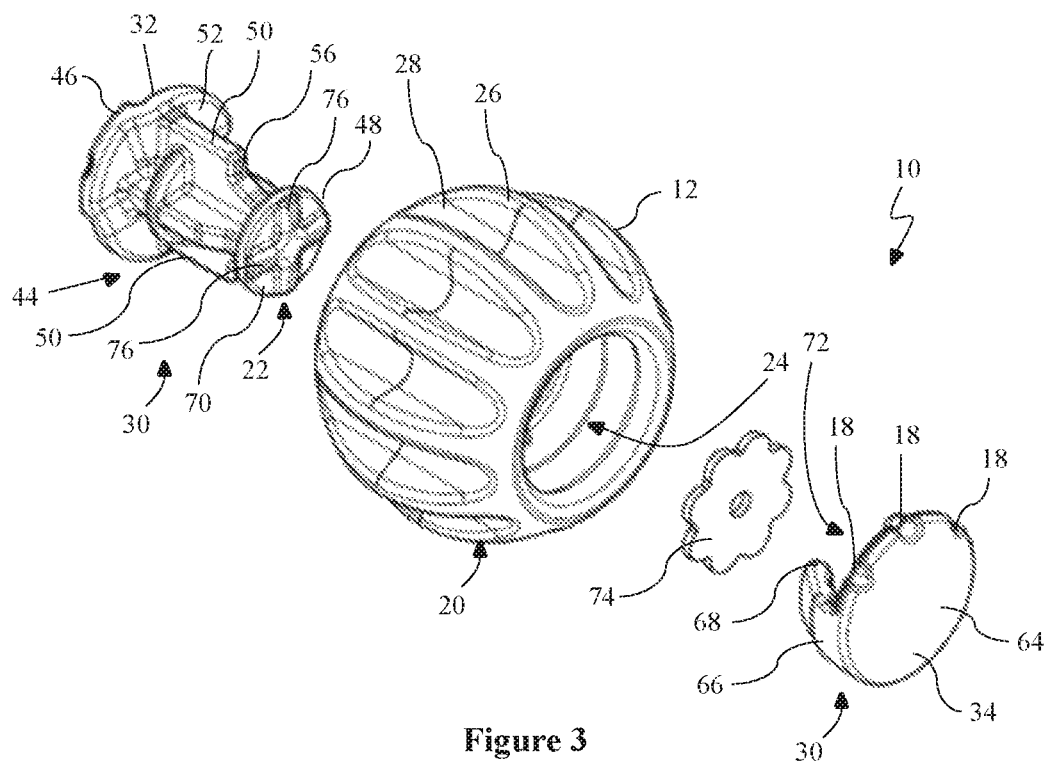
FIG. 3 is an exploded isometric view of an animal training aid or toy in accordance with an embodiment of the invention.
Figure 4:
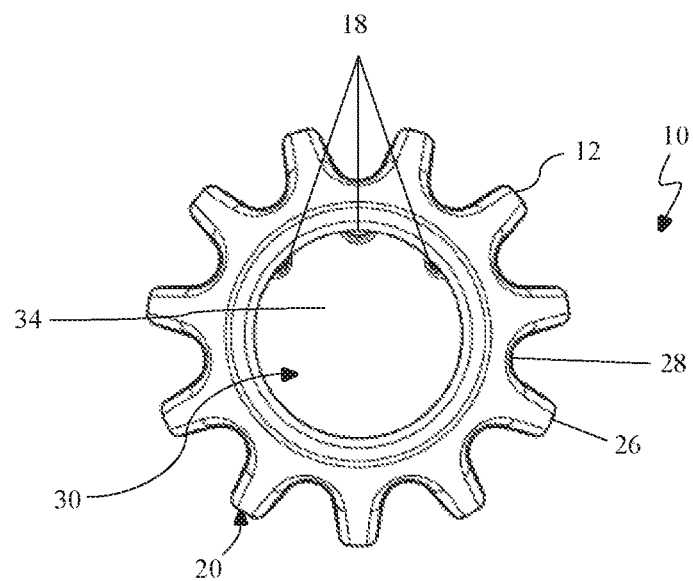
FIG. 4 is a plan view from one end of an animal training aid or toy in accordance with an embodiment of the invention.
Figure 5:
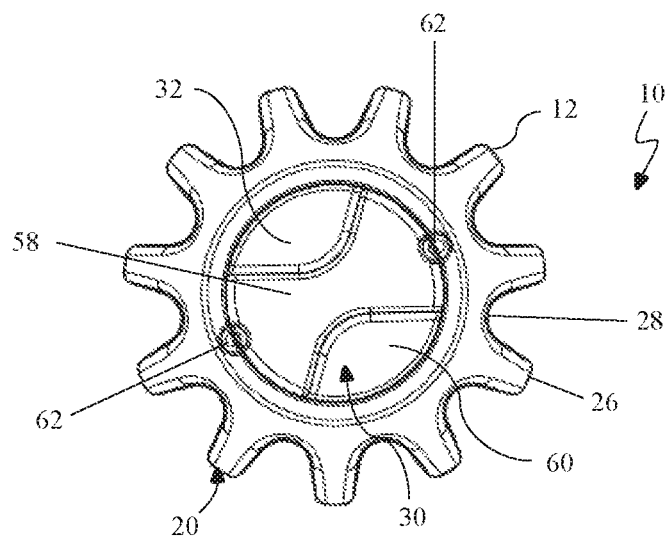
FIG. 5 is a plan view from another end of an animal training aid or toy in accordance with an embodiment of the invention.
Figure 6:
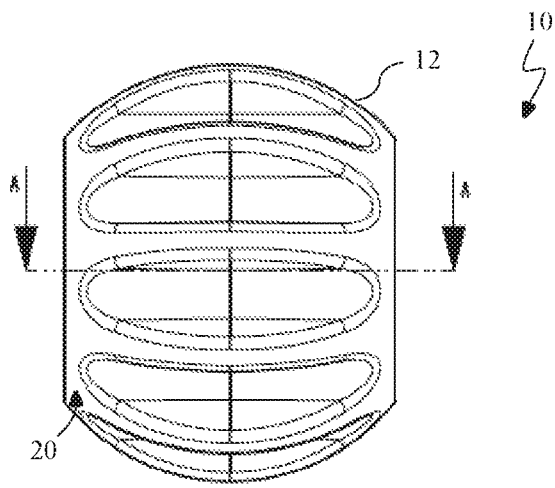
FIG. 6 is a side view of an animal training aid or toy in accordance with an embodiment of the invention.
Figure 7:
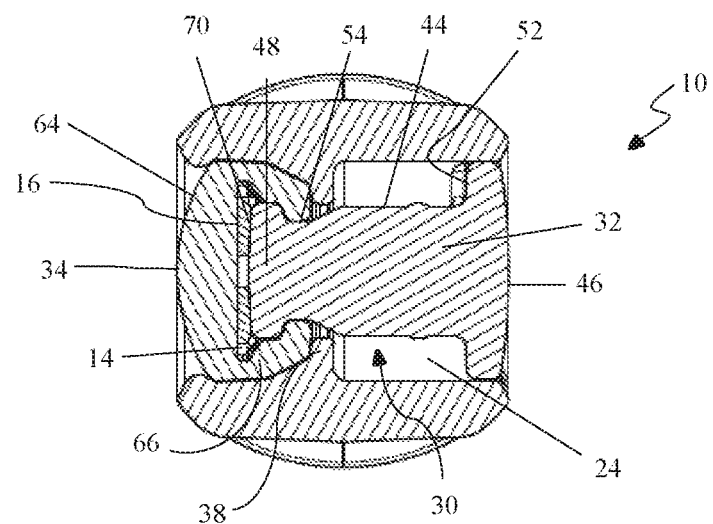
FIG. 7 is a cross section view through A-A of FIG. 6.
Figure 8:
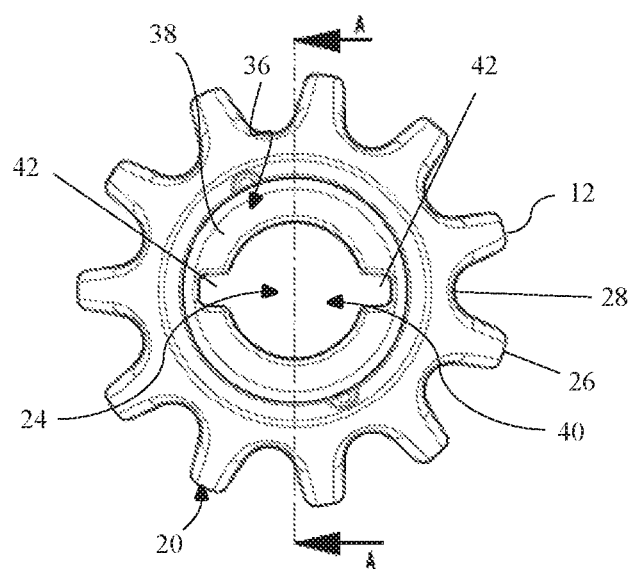
FIG. 8 is a plan view from an end of an animal training aid or toy in accordance with an embodiment of the invention.
Figure 9:
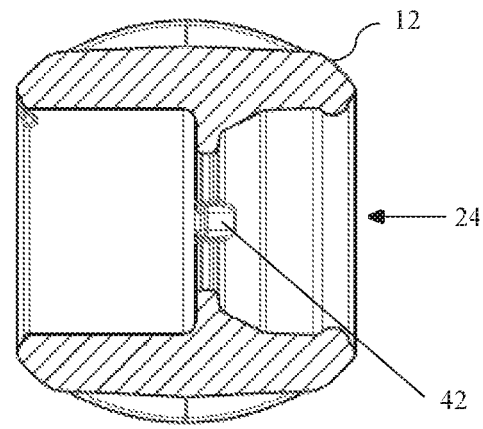
FIG. 9 is a cross section view through A-A of FIG. 8.
Figure 10:
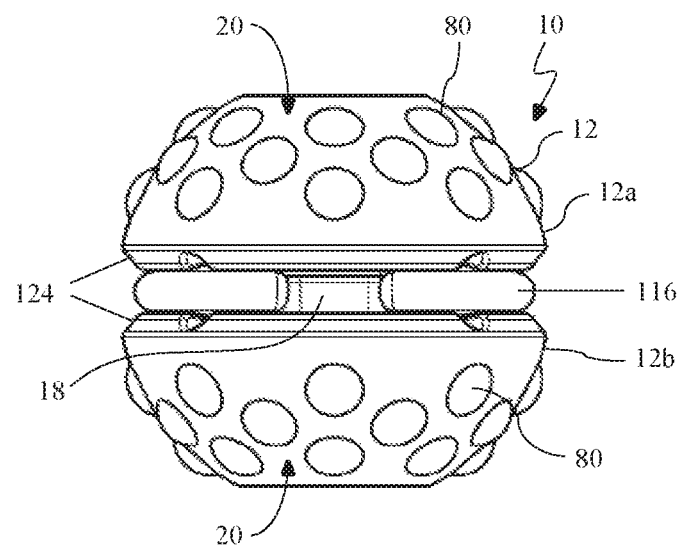
FIG. 10 is a side view of an animal training aid or toy in accordance with a further embodiment of the invention.
Figure 11:
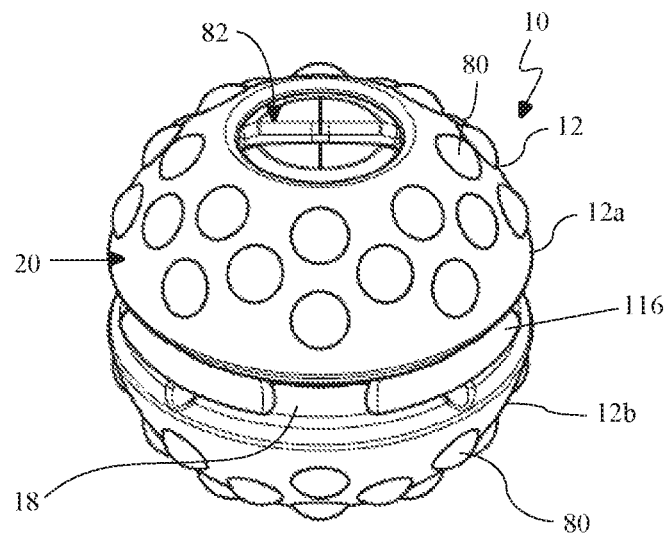
FIG. 11 is an isometric view of an animal training aid or toy in accordance with the further embodiment of the invention.
Figure 12:
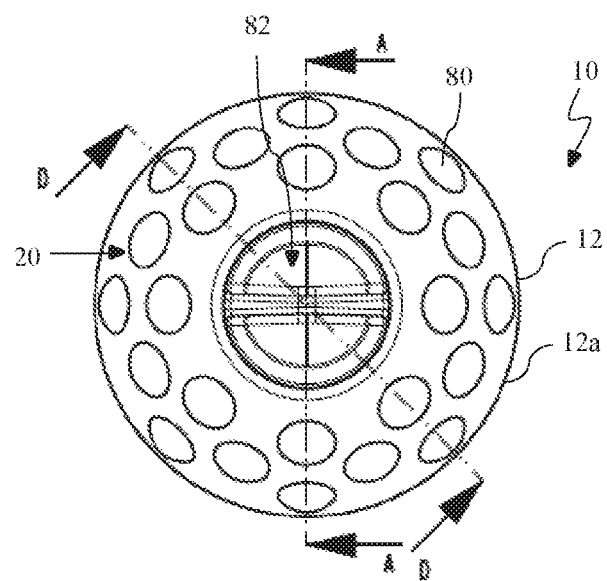
FIG. 12 is a plan view from the top of an animal training aid or toy in accordance with the further embodiment of the invention.
Figure 13:
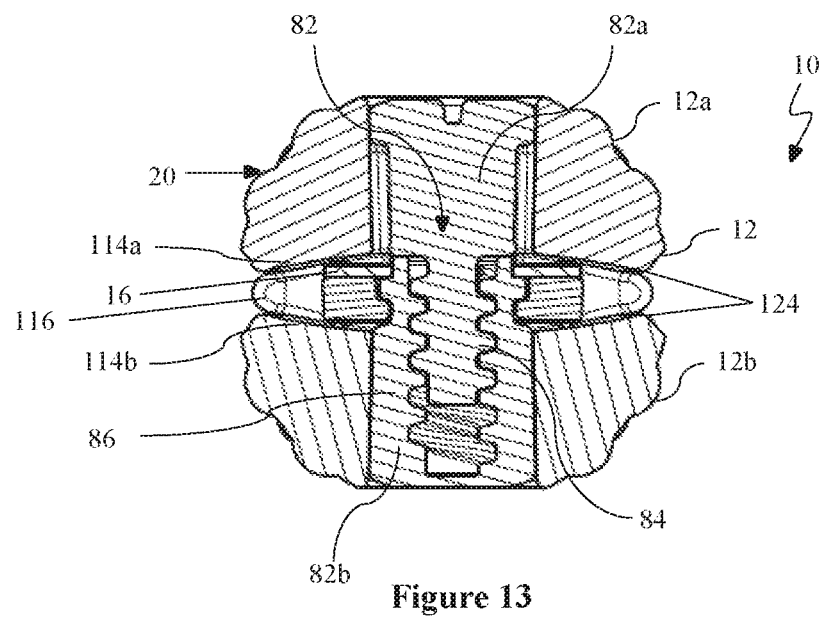
FIG. 13 is a cross section view through A-A of FIG. 10.
Figure 14:
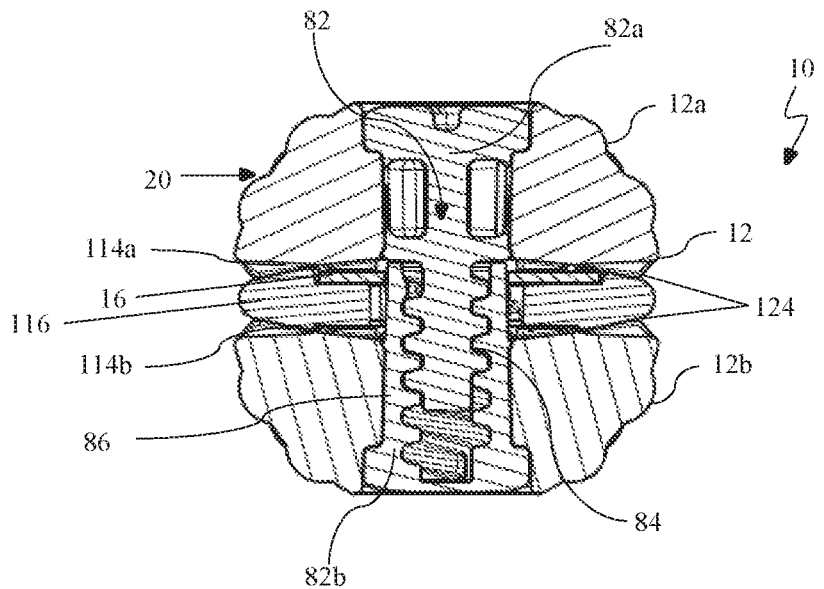
FIG. 14 is a cross section view through D-D of FIG. 10.
Figure 15:
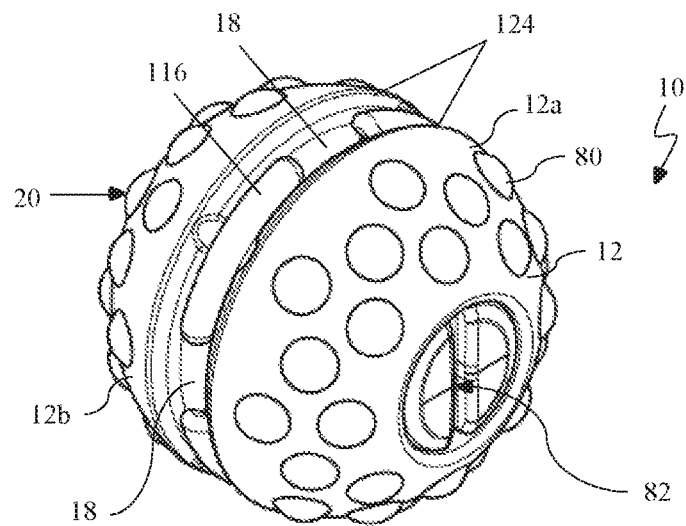
FIG. 15 is an isometric view of an animal training aid or toy in accordance with the further embodiment of the invention.
Figure 16:
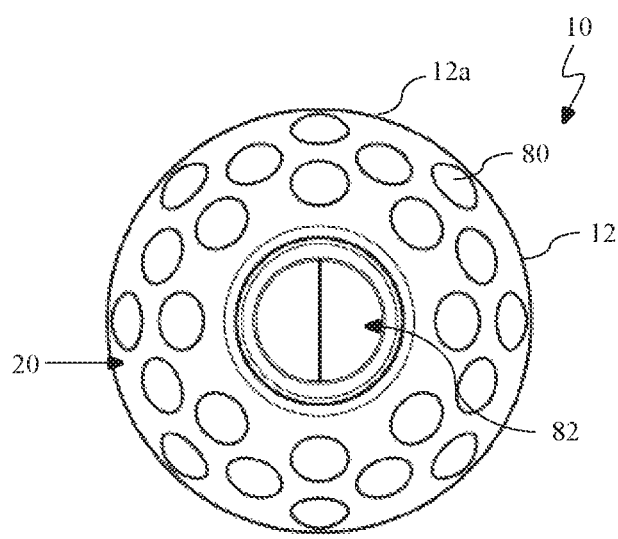
FIG. 16 is a plan view from below of an animal training aid or toy in accordance with the further embodiment of the invention.
Figure 17:
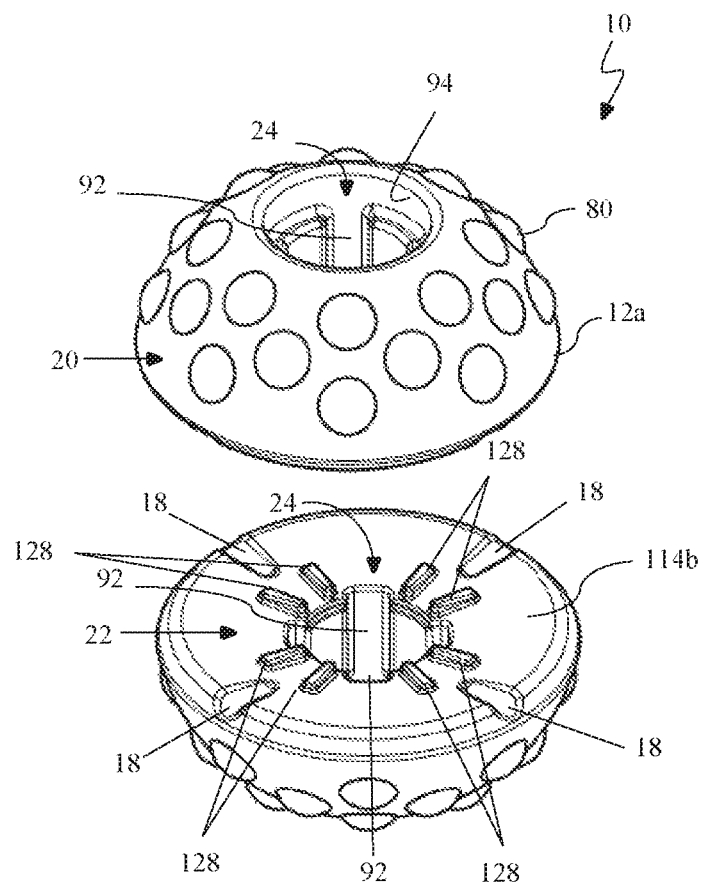
FIG. 17 is an exploded isometric view of two housing parts of an animal training aid or toy in accordance with the further embodiment of the invention.
Figure 18:
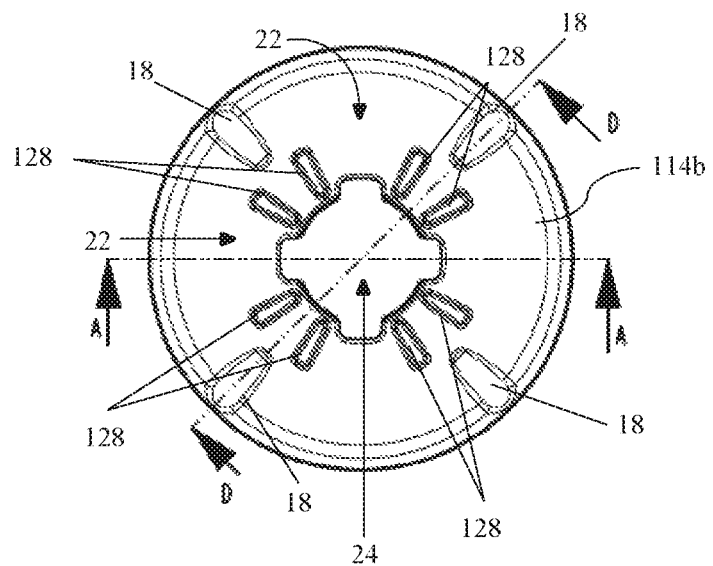
FIG. 18 is a plan view from the top of a housing part of an animal training aid or toy in accordance with the further embodiment of the invention.
Figure 19:
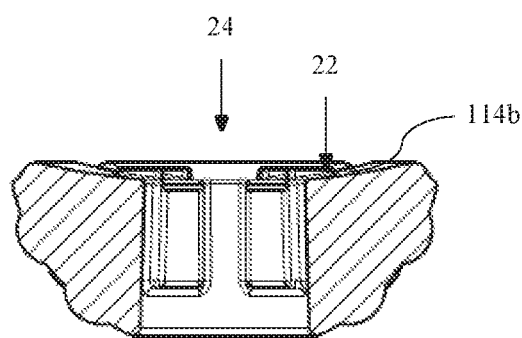
FIG. 19 is a cross section view through A-A of FIG. 16.
Figure 20:
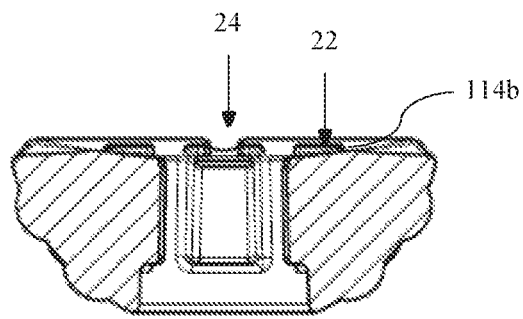
FIG. 20 is a cross section view through D-D of FIG. 16.
Figure 21:
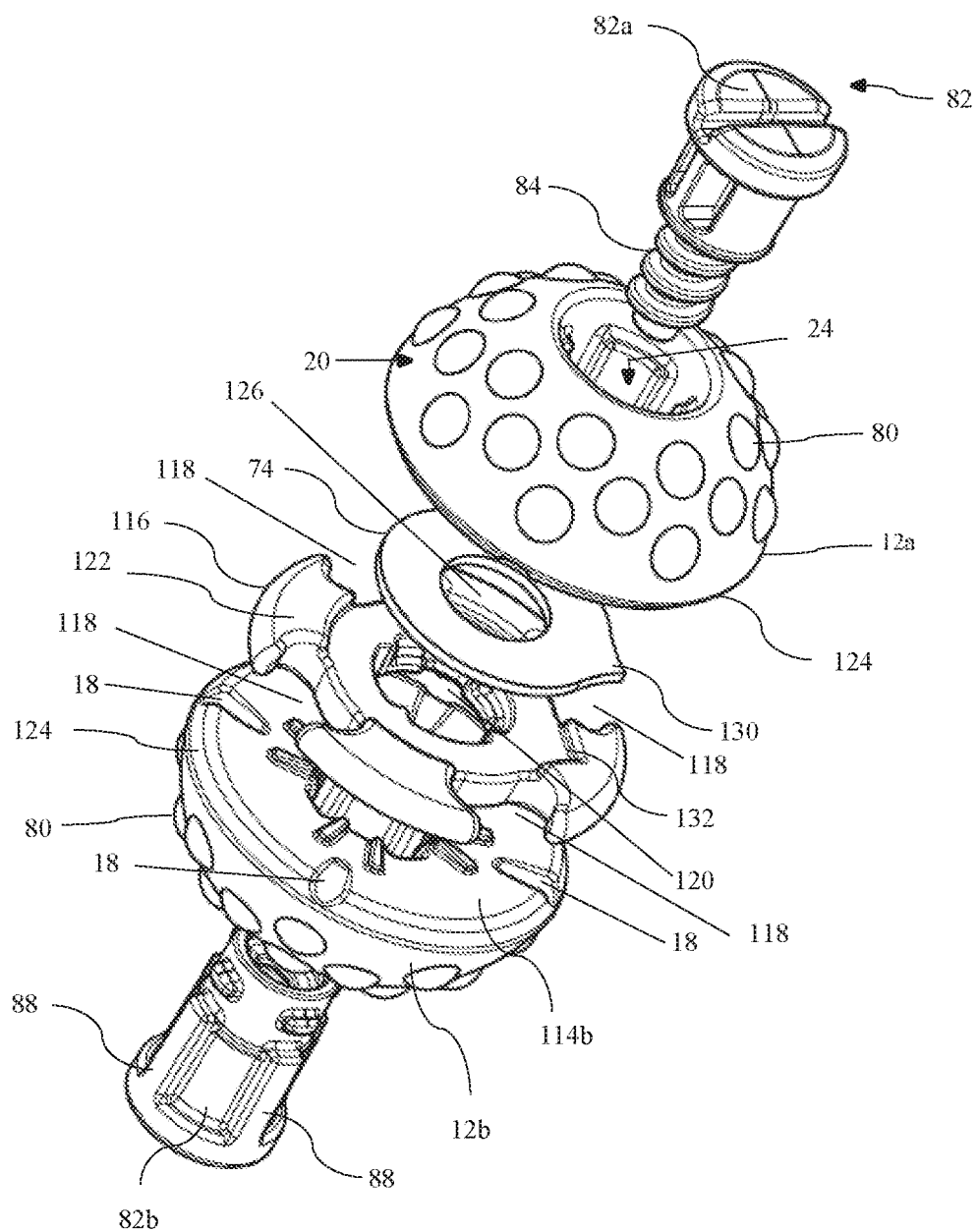
FIG. 21 is an exploded isometric view of an animal training aid or toy in accordance with the further embodiment of the invention.
Figure 22:
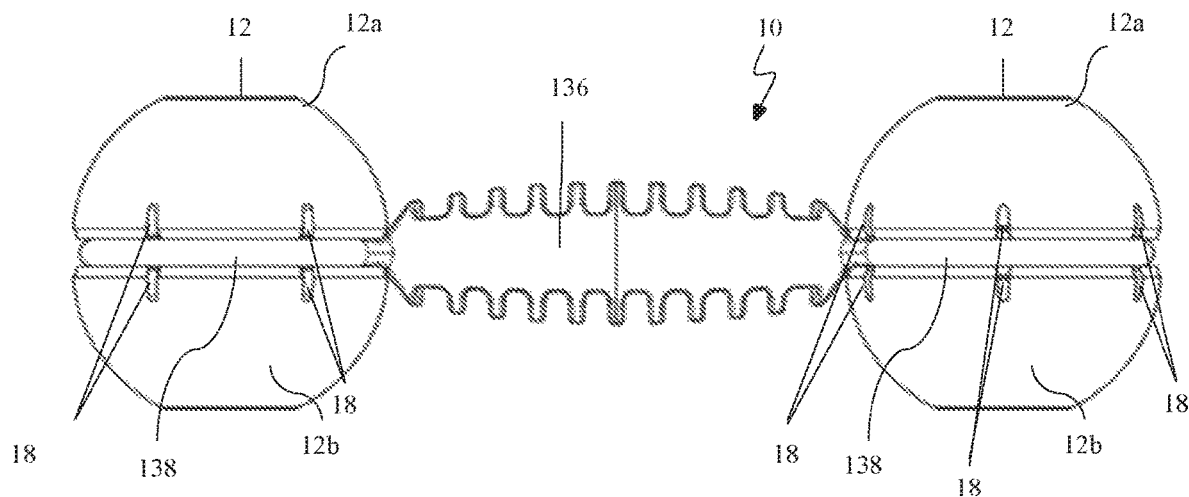
FIG. 22 is a side view of an animal training aid or toy in accordance with another embodiment of the invention.
Figure 23:
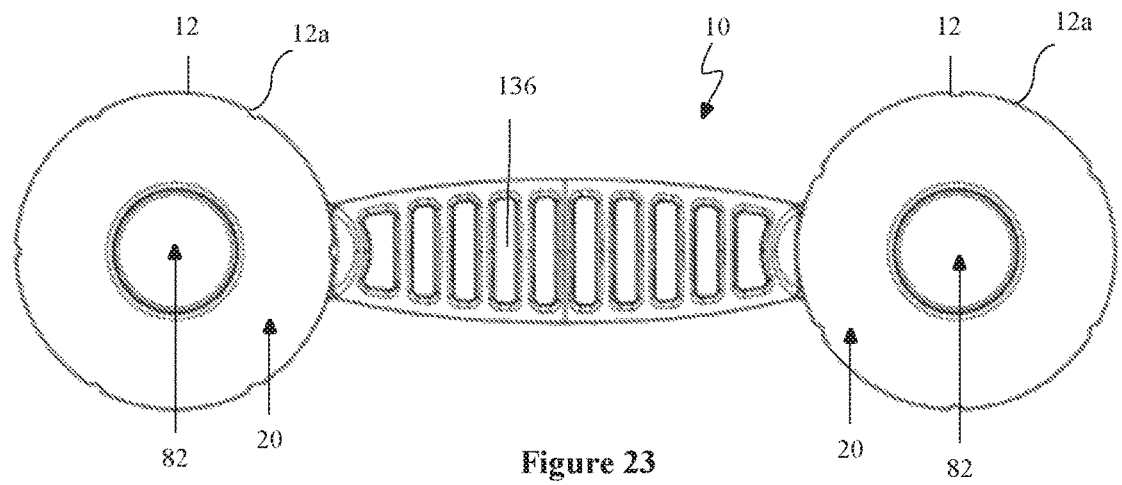
FIG. 23 is a plan view of an animal training aid or toy in accordance with the other embodiment of the invention.
Figure 24:
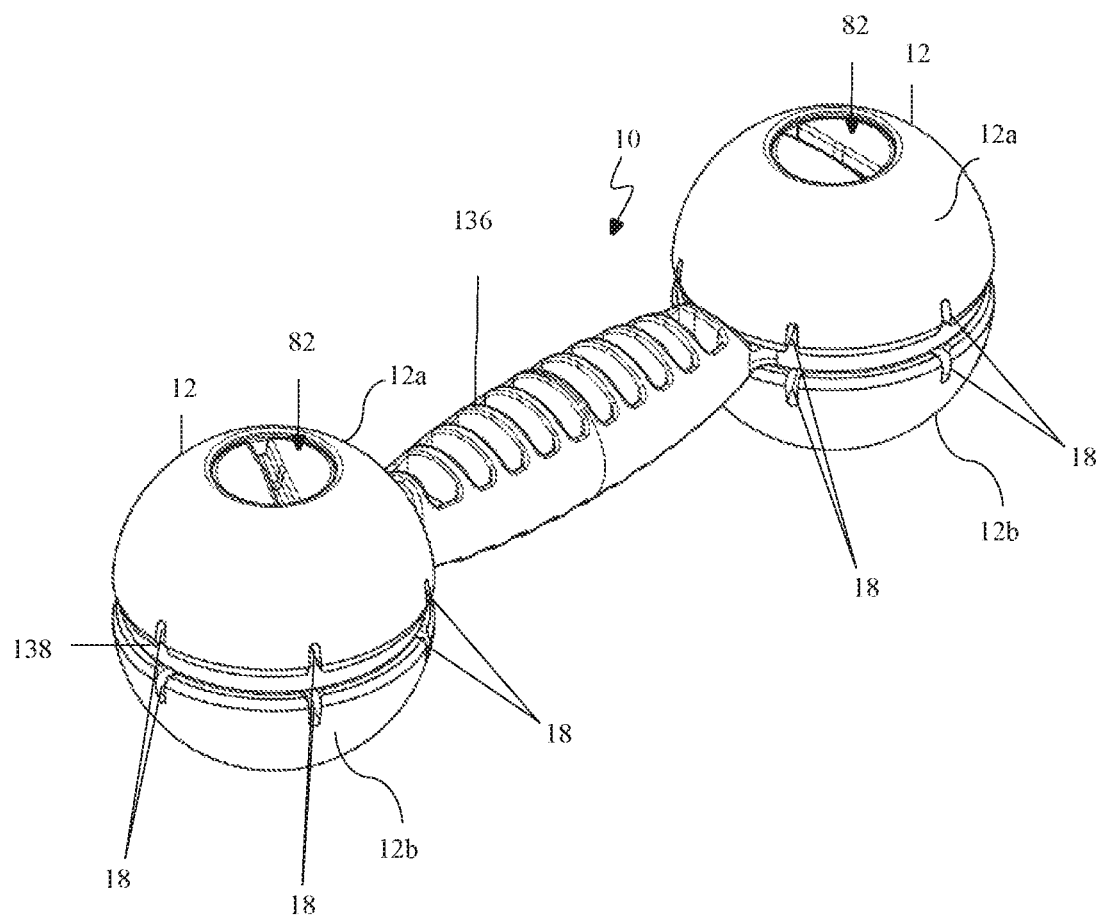
FIG. 24 is an isometric view of an animal training aid or toy in accordance with the other embodiment of the invention.
Figure 25:
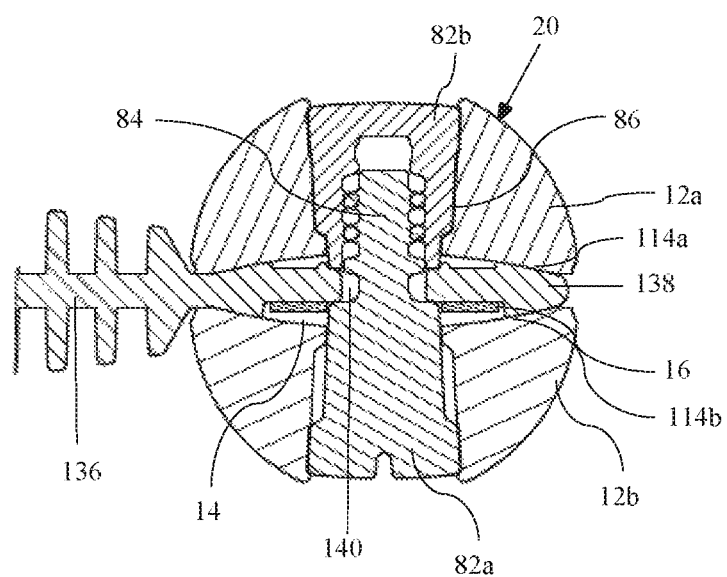
FIG. 25 is a cross section view of part of an animal training aid or toy in accordance with the other embodiment of the invention.

In use, the plug and cap assembly 30 is retained in the central bore 24 by a retainer 36. Details of the retainer 36 are best seen in FIGS. 7 and 8, where it can be seen that the central bore 24 comprises a reduced diameter annular flange 38 in the bore 24. The flange 38 defines a reduced diameter aperture 40 in the bore. The diameter of the aperture 40 is less than the mean or average internal diameter of the central bore 24. The reduced diameter annular flange 38 is used to retain the plug and cap assembly 30 in the central bore 24 when the toy 10 is in use. Specifically, the annular flange 38 retains the plug and cap assembly 30 using a "lock and key" system. The annular flange 38 comprises one or more slots 42 that extend radially outwardly in the flange 38. As best seen in FIG. 8, in the illustrated embodiment there are two slots 42 but the skilled person will appreciate that any number of slots 42 (i.e. one or more) could be used. The plug 32 comprises a generally elongate body 44 and larger diameter first 46 and second 48 end sections. The body 44 comprises two wall sections 50, each of which extends radially outwardly from the body 44. The wall sections 50 extend from an underside surface 52 of the first end section 46 longitudinally along the body 44 but do not extend all the way to the second end section 48. Thus, there is a reduced diameter section 54 of the body 44 adjacent the second end section 48. In use, the plug 32 is inserted in the central bore 24 until a bearing surface 56 at the end of each of the wall sections 50 bears against the flange 38. At this point the plug 32 is housed entirely within the central bore 24. The diameter of the first end section 46 of the plug 32 is slightly less than the diameter of the central bore 24 so that when the plug 32 is housed within the bore 24 the first end section effectively closes off the bore 24 when viewed from the surface of the toy 10, as shown in FIG. 5. The plug 32 can be rotated freely within the bore 24 in this configuration.

The plug 32 can be rotated within the bore 24 to a position in which the wall sections 50 are aligned or coincident with the slots 42. In this position, the first end section 46 can be pushed further into the bore 24 with the wall sections 50 travelling within slots 42. As the first end section 46 is pushed further into the bore 24, the second end section 48 emerges from the bore 24 at the opposing end of the bore 24. This then allows physical access to the second end section 48 of the plug 32 when the plug 32 is housed in the bore 24. To assist a user in rotating the plug 32 within the bore 24, the first end section contains a handle 58 that protrudes from an external surface 60 of the first end section 46. A user can grip the handle 58 between their thumb and forefinger to rotate the plug 32 within the bore 24. To enable a user to know when the wall sections 50 are aligned with the slots 42, the external surface 60 of the first end section 46 and the exterior surface 20 of the housing 12 contain indicia 62 to indicate when the wall sections 50 are aligned with the slots 42.

When the second end section 48 of the plug 32 extends from the bore 24 the plug and cap assembly 30 can be assembled and disassembled by fitting or removing the cap 34 from the second end section 48. The cap 34 comprises a base 64 and a retaining flange 66 extending from one face of the base 64. The retaining flange 66 is arcuate in cross section and is shaped so that the second end section 48 of the plug 32 is able to fit into the cap 34 such that it is positioned adjacent the face of the base 64 from which the flange 66 extends. A free edge section 68 of the retaining flange 66 has a smaller diameter than the diameter of the second end section 48 so that, when assembled, the free edge section 68 bears against a surface 70 of the second end section 48 so that the cap 34 cannot be removed from the plug 32 by applying a longitudinal force in the direction of the longitudinal axis of the plug 32. In other words, the cap 34 is fitted and removed from the plug 32 by moving toward or away from the second end section 48 in a direction that is substantially lateral to a longitudinal axis of the plug 32. Once the cap 34 is fitted to the plug 32, the plug and cap assembly 30 can be pushed back into the bore 24 so that the entire plug and cap assembly 30 is housed in the bore 24. In this configuration, the cap 34 cannot be removed from the plug 32 because movement of the cap 34 laterally to a longitudinal axis of the plug is prevented because the cap 32 is housed in the bore 24.

In the illustrated embodiments, the cap 34 is generally circular in cross section and the retaining flange 66 is semi-circular. There is a gap 72 in the retaining flange through which the second end section 48 of the plug 32 passes when the cap 34 is fitted or removed from the plug 32.

As best seen in FIG. 7, the plug and cap assembly 30 forms the interior cavity 14 in which the scented material 16 is located. The cap 34 comprises vents 18. The vents are in the form of notches in the periphery of the cap. The vents 18 allow scents from the scented material 16 to be released to the exterior of the toy 10 when the scented material 16 is activated.

It will be appreciated that other forms and configurations of plug 32 and cap 34 could also be used provided they are not able to be disassembled when the plug and cap assembly 30 is housed in the bore 24.

Optionally, the base 64 of the cap 34 may be transparent and this allows a user to see whether scented material 16 is present in the interior cavity 14 without having to disassemble the toy 10. A transparent base 64 also allows a user to read any indicia or writing on the scented material 16 which may, for example, identify the scent (e.g. beef, fish, etc) on the scented material 16.

Optionally, the plug 32 may contain an extension (not shown) that protrudes from the first end section 46 and extends from the aid or toy 10 when the plug and cap assembly 30 is housed in the bore 24. The extension may be used to attach the aid or toy 10

The scented material 16 may be a liquid scent, such as an oily scent, or a solid having a liquid scent imbibed therein or thereon. In the illustrated embodiments, the scented material 16 is a solid and is in the form of a scented disc 74 having a scented liquid or oil imbibed therein or thereon. The scented liquid or oil is microencapsulated and the microencapsulated particles are then applied to the surface of the disc 74. In an unactivated state, most of the microencapsulated particles are intact and substantially no scent (as previously defined) is released from the disc 74. Upon activation, a substantial number of the microencapsulated particles are broken or otherwise disrupted so that the scented oil or liquid contained therein is exposed and the volatile scent components are released. The disc 74 can be made from an absorbent material that is porous enough to absorb a liquid or oily scent. Many absorbent materials can be used, including cardboard, card, ceramics, zeolites, porous plastics, foams and sponges. Recycled, biodegradable card stock is a particularly suitable porous material for this purpose. The scent may be any liquid or oily material that contains a scent that is attractive to the animal. For dogs, chicken, beef, bacon, ham or salmon scents can be used. Other scents such as pheromones and other materials that sooth or pacify animals could also be used. These scents are available commercially.

The scented disc 74 can be positioned in the interior cavity 14. The scent is imbibed internally in the disc 74 which has a thin outer coating that prevents release of a scent from the disc 74 until it has been activated by removing at least part of the outer coating. The scented disc 74 is activated by the activator 22 which, in the embodiments illustrated in FIGS. 1 to 9 is in the form of one or more ribs 76 (best seen in FIG. 3) that protrude from the end surface 70 of the second end section 48 of the plug 32. Rotation of the plug 32 using the handle 58 results in the rib(s) 76 abrading the surface of the disc 74 to remove at least some of the outer coating thereon to thereby activate the disc 74 so that the imbibed scent is released therefrom.

Advantageously, the cap 34 may also be used on other devices such as leads, wrist bands, blankets, bedding, etc. For example, the aid or toy 10 could be incorporated into an animal's bedding. In another example, the other devices may comprise a protrusion that is in the same form as the second end section 48 of the plug 32. In use, the scented material 16 may be placed in the cap 34 and the cap attached to the protrusion on the device. This allows for the cap 34 to be used with a range of devices.

In the embodiment illustrated in FIGS. 10 to 21, the housing 12 comprises a plurality of housing parts 12a and 12b that are separable from one another to allow the scented material 16 to be introduced or removed from the interior cavity 14. In these embodiments, the housing 10 comprises two substantially hemispherical housing parts 12a and 12b. Each housing part 12a and 12b comprises a central bore 24 that extends from the exterior surface 20 to the interior cavity 14. In these embodiments, the exterior surface 20 of the housing parts 12a and 12b comprises a plurality of domed protrusions 80 that assist a handler or the animal with gripping the aid or toy 10. Other decorative or functional forms could be included on the exterior surface. In the embodiments shown in FIGS. 22 to 25, the exterior surface 20 of the housing parts 12a and 12b is substantially smooth.

The aid or toy 10 also comprises a retainer 82 for holding the two housing parts 12a and 12b together. The retainer 82 comprises two retainer parts 82a and 82b. One of the retainer parts 82a comprises a male threaded section 84 and the other retainer part 82b comprises a female threaded section 86. The retainer parts 82a and 82b can be fitted into the bore 24 in respective housing parts 12a and 12b. The male threaded section 84 can be threaded into the female threaded section 86 to retain the housing parts 12a and 12b together to form the assembled aid or toy 10 and unthreaded from one another to provide access to the interior cavity 14. The bores 24 are tapered inwardly from the exterior surface 20 toward the interior cavity 14 and each retainer part 82a and 82b has a taper that is substantially complementary to the taper of the bores 24. At least one of the retainer parts 82a and 82b is also keyed to the corresponding bore 24 of the housing part 12a or 12b to prevent rotation between the retainer part 82a/82b and the housing part 12a/12b. Specifically, as seen in FIGS. 14 and 19-21 the retainer part 82b comprises at least one longitudinal protrusion 88 extending from an external surface 90 and at least one corresponding longitudinal recess 92 formed on an internal surface 94 of the bore 24 in housing part 12b. The protrusion 88 and recess 92 are substantially complementary in shape and size with respect to one another such that the protrusion 88 can be fitted in to the recess 92 to form a keyed arrangement between the retainer part 82b and housing part 12b or between the retainer part 82b and housing part 12b and prevent mutual rotation between respective retainer parts 82a/82b and housing parts 12a/12b.

In other embodiments that are illustrated in FIG. 26, the retainer 82 for holding the two housing parts 12a and 12b together is in the form of clips 96. The clips 96 comprise hook members 98 extending from housing parts 12a and 12b. The hook members 98 each comprise a post 100 and a hook portion 102. The hook portion 102 comprises a sloped surface 104 and a retaining surface 106. A central joiner ring 108 comprises cavities 110 into which the hook portion 102 of each hook member 98 fits when the two housing parts 12a and 12b are fitted together with the central joiner ring 108 in between. Each post 100 is resiliently flexible so that when the two housing parts 12a and 12b are brought into engagement with the central joiner ring 108 a surface of each cavity 110 bears on the sloped surface 104 of a respective hook member 98, resulting in the hook members 98 flexing toward one another to allow entry of each hook portion 102 into the respective cavity 110. When the hook portion 102 is fully inserted into cavity 110 the hook members 98 snap back into their original position and the retaining surface 106 of each hook member 98 bears against a ridge 112 in the cavity 110 to lock the housing parts 12a and 12b together.

In the embodiments illustrated in FIGS. 10 to 25, the interior cavity 14 is formed by two arcuate internal surfaces 114a and 114b on the housing parts 12a and 12b when the housing 12 is assembled. A scented material retainer 116 is positioned between the two housing parts 12a and 12b. The scented material retainer 116 is plate like and generally circular in cross section and has a plurality of peripheral cut outs 118 extending radially inwardly from the periphery. When the aid or toy is assembled the cut outs 118 provide further vents 18 through which a scent from the scented material 16 can be released from the interior cavity 14 to the exterior of the housing 12. The scented material retainer 116 also comprises a central aperture 120 through which the retainer parts 82a and 82b pass when the aid or toy 10 assembled. A scented disc 74 can be positioned in a disc receiving depression 122 formed in one face of the scented material retainer 116. The disc receiving depression 122 has the same general shape as the scented annular disc 74.

A peripheral edge 124 of each of the housing parts 12a and 12b contacts the periphery of the scented material retainer 116 when the housing 12 is assembled to effectively seal the periphery of the two housing parts 12a and 12b. The vents 18 are open to the interior cavity 14 and the exterior of the housing 12 to allow passage of a scent from the scented material 16 from the interior cavity 14 to the outside of the aid or toy 10.

As described previously, the scented material 16 may be a liquid scent, such as an oily scent, or a solid having a liquid scent imbibed therein or thereon. In the illustrated embodiments, the scented material 16 is a solid and is in the form of a scented disc 74 having a scented liquid or oil imbibed therein or thereon, as previously described.

The scented disc 74 can be positioned in the interior cavity 14 with the retainer parts 82a and 82b passing through a central aperture 126 in the scented disc 74. The scent is imbibed internally in the disc 74 which has a thin outer coating that prevents release of a scent from the disc 74 until it has been activated by removing at least part of the outer coating. The scented annular disc 74 is activated by the activator 22 which, in the embodiments illustrated in FIGS. 10 to 25 is in the form of one or more ribs 128 (best seen in FIGS. 17 to 21) that protrude from at least one of the internal surfaces 114a or 114b. The rib(s) 128 contact at least one surface of the disc 74 when the housing 12 is assembled and rotation of one of the housing parts 12a relative to the other one 12b results in the rib(s) 128 abrading the surface of the disc 74 to remove at least some of the outer coating thereon to thereby activate the disc 74 so that the imbibed scent is released therefrom. The periphery of the disc 74 has a key section 130 which extends radially from the periphery. The disc receiving depression 122 on the scented material retainer 116 has a key section 132 which is complementary in shape to the key section 130 on the disc 74. To install a disc 74 into the aid or toy 10, the housing parts 12a and 12b are separated from one another and a disc 74 is positioned on the scented material retainer 116 so that the key section 130 fits in to the key section 132. In this way, the disc 74 is unable to rotate relative to the scented material retainer 116. The male threaded section 84 of retainer part 82a is inserted into the apertures 120 and 126.

In the embodiments illustrated in FIGS. 22 to 25, the aperture 126 in the scented disc 74 has key cut out sections (not shown) which key to protrusions (not shown) on the retainer part 82a to prevent rotation of the disc 74 relative to the retainer part 82b. Thus, an alternative form of keyed arrangement is formed between the retainer part 82a and the disc 74 which prevents the latter from rotating relative to the retainer part 82a and, hence, the housing part 12a.

In other embodiments that are not illustrated, the scented material 16 may form of a capsule containing a scented liquid or oil. The capsule can be placed in the interior cavity 14 of the aid or toy 10. The activator 22 can then be used to pierce or crush the capsule so that the capsule is opened and the scented liquid or oil is released therefrom. For example, one or both of the housing parts 12a and 12b or the cap 34 may be elastically deformable so that it can be depressed to activate the capsule in the interior cavity 14. In these embodiments, the interior cavity 14 may contain an absorbent material, such as a sponge material, onto which the liquid scented material is or can be absorbed.

In some embodiments, the aid or toy 10 further comprises attachment means 134 for removably attaching the housing 12 to a substrate or device 136 such as a wrist band, lead, toy or similar. These embodiments provide a modular system in which a single housing 12 can be attached and removed from a range of training aids (e.g. wrist band or lead) and/or toys (e.g. bone or toy animal). The attachment means 134 may be in the form of a key and slot arrangement with a slot on the housing 12 and a corresponding key on the device 136, or vice versa.

In embodiments that are shown in FIGS. 22 to 25, the aid or toy 10 can be attached to a substrate or device 136 such as a larger toy or training aid. Illustrated is a device 136 in the general shape of a bone. Ends 138 of the device 136 are flattened and circular and comprise a central aperture 140. The aid or toy 10 illustrated in FIGS. 10 to 21 can be attached to the ends 138 to form a training aid or toy in the form of a scented bone. In the illustrated embodiments, the aid or toy 10 attached to the ends 138 is similar to the aid or toy 10 shown in FIGS. 10 to 21 but has a substantially smooth exterior surface 20. As with the aid or toy 10 shown in FIGS. 10 to 21, the ball part of the aid or toy 10 shown in FIGS. 22 to 25 comprises housing parts 12a and 12b that can be separated from one another and the male threaded section 84 of the retainer part 82a inserted through the aperture 140 and the corresponding housing part 12a can then be threaded into the female threaded section 86, as described earlier. In this way, the aid or toy 10 can be attached to the device 136. The device 136 can be any shape and could, for example, be a lead having a flattened section with an aperture through which the aid or toy 10 can be attached as just described.

In embodiments that are not illustrated, the one or more vent(s) 18 can be opened and closed such that when the vent(s) 18 are open the scent from the scented material is released from the interior cavity 14 to the exterior of the housing 12 and when the vent(s) 18 are closed the scent is substantially contained within the interior cavity 14.

According to a second aspect, there is provided a method for training animals using primary reinforcement to reinforce desired animal behaviour, the method comprising: providing an animal training aid or toy in accordance with the present invention; activating the scented material in the aid or toy; and providing a reward to the animal simultaneously with, or immediately following, a desired behaviour by providing the animal with the aid or toy.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. An animal toy comprising:
   a housing adapted for animal play or chewing activities, the housing comprising a bore extending through the housing; an interior cavity provided within the bore and configured to contain a disc comprising a microencapsulated scent thereon; and
   one or more vents, wherein the interior cavity is in fluid communication with an exterior of the housing via the one or more vents so that the scent from the disc can be released from the interior cavity to the exterior of the housing where it can be detected by the animal; and
   an activator for activating the disc from an unactivated state to an activated state, the activator comprising a plurality of protrusions operable to abrade a surface of the disc to rupture at least some microcapsules to activate the disc and release the scent and further operable to abrade the surface of the disc to rupture further microcapsules to increase the amount of scent released, the activator being operable from the exterior of the housing;
   wherein the disc releases substantially no scent that is desirable to the animal in the unactivated state and releases the scent that is desirable to the animal in the activated state in which the animal toy can be used in scent based animal activities.

2. The animal toy according to claim 1, wherein the housing is a unitary construction.

3. The animal toy according to claim 1, wherein the bore comprises the interior cavity.

4. The animal toy according to claim 3, wherein the animal toy also comprises a plug and a cap used to retain the disc in the interior cavity in the bore.

5. The animal toy according to claim 4, wherein the plug is removable from and insertable into the bore.

6. The animal toy according to claim 4, wherein the cap is removable from and insertable into the bore.

7. The animal toy according to claim 6, wherein, in use, the plug and cap are retained in the bore by a retainer.

8. The animal toy according to claim 4 wherein the cap retains the disc.

9. The animal toy according to claim 4, wherein the cap contains the one or more vents.

10. The animal toy according to claim 4 wherein the plug comprises the activator.

11. The animal toy according to claim 10, wherein the plug is rotatable.

12. The animal toy according to claim 11, wherein when the disc is contained in the bore, rotation of the plug causes the activator to activate the disc to the activated state the scent to be released through the one or more vents.

13. The animal toy according to claim 4, wherein the plug and cap fit together to define a plug and cap assembly.

14. The animal toy according to claim 4, wherein when the toy is in an assembled condition, the plug has a first end located in the bore, the disc is located between the first end of the plug and the cap, and the plug is rotatable relative to the cap to activate the disc from the unactivated state to the activated state.

15. The animal toy according to claim 14, wherein the plurality of protrusions are formed on the first end of the plug and positioned in contact with the disc.

16. The animal toy according to claim 1, wherein the bore is positioned centrally in the housing and extends diametrically through the housing.

17. A method for training animals using primary reinforcement to reinforce desired animal behaviour, the method comprising: providing an animal toy in accordance with claim 1; activating the scented material in toy; and providing the animal with the toy to reward the animal simultaneously with, or immediately following, a desired behaviour.

* * * * *